US008591227B2

(12) United States Patent
Levine

(10) Patent No.: US 8,591,227 B2
(45) Date of Patent: *Nov. 26, 2013

(54) MOUTHPIECE THAT ADJUSTS TO USER ARCH SIZES AND SEALS FROM OXYGEN EXPOSURE

(75) Inventor: Jonathan B. Levine, Purchase, NY (US)

(73) Assignee: JBL Radical Innovations, LLC

(*) Notice: Subject to any disclaimer, the term of this patent is extended or adjusted under 35 U.S.C. 154(b) by 0 days.

This patent is subject to a terminal disclaimer.

(21) Appl. No.: 13/374,484

(22) Filed: Dec. 30, 2011

(65) Prior Publication Data

US 2012/0183919 A1 Jul. 19, 2012

Related U.S. Application Data

(63) Continuation-in-part of application No. 12/246,012, filed on Oct. 6, 2008, now abandoned.

(51) Int. Cl.
*A61C 1/00* (2006.01)
*A61C 3/00* (2006.01)
(52) U.S. Cl.
USPC .................. 433/29; 433/32; 433/215

(58) Field of Classification Search
USPC .................. 433/29, 80, 89, 215, 32
See application file for complete search history.

(56) References Cited

U.S. PATENT DOCUMENTS

| | | | |
|---|---|---|---|
| 6,860,879 B2 * | 3/2005 | Irion et al. | 606/16 |
| 7,107,996 B2 * | 9/2006 | Ganz et al. | 128/898 |
| 7,320,595 B2 * | 1/2008 | Duret | 433/32 |
| 2005/0202363 A1 * | 9/2005 | Osterwalder | 433/29 |
| 2006/0019214 A1 * | 1/2006 | Lawrence et al. | 433/29 |
| 2006/0078848 A1 * | 4/2006 | Fischer et al. | 433/215 |
| 2007/0212661 A1 * | 9/2007 | Mehmet | 433/32 |
| 2007/0259316 A1 * | 11/2007 | Conrad et al. | 433/215 |
| 2008/0003540 A1 * | 1/2008 | Khawaled et al. | 433/215 |

* cited by examiner

*Primary Examiner* — Eric Rosen
(74) *Attorney, Agent, or Firm* — H. Jay Spiegel

(57) ABSTRACT

A mouthpiece that adjusts manually to accommodate a broad range of different size sets of upper and lower teeth in the mouth and yet seals the treatment area from oxygen exposure. The mouthpiece includes light emitting diodes and heat generating resistors all arranged in an array. A series of parallel texture bands are provides to guide and direct the light from the LEDs to diffuse generally evenly onto teeth to be treated. The seal arises from an inner surface of the mouthpiece titling inwardly so that a seal bead seals in the vicinity of the gum above the teeth to be treated.

19 Claims, 3 Drawing Sheets

MOUTHPIECE THAT ADJUSTS TO USER ARCH SIZES AND SEALS FROM OXYGEN EXPOSURE

This application is a Continuation-in-Part of application Ser. No. 12/246,012, filed on Oct. 6, 2008 now abandoned.

BACKGROUND OF THE INVENTION

1. Field of the Invention

The present invention relates to a mouthpiece containing lamps and heat resistors to expose electromagnetic radiation to effect oral treatment and, specifically, to aid the activation of an adhesive whitening gel to whiten teeth. The present invention may also be used to kill harmful bacteria in the mouth through the electromagnetic radiation exposure and the activation of various formulations. The mouthpiece adjusts manually to accommodate a broad range of user sizes, yet seals the treatment area from oxygen escape.

2. Description of Related Art

Conventional teeth whitening in the dental office takes up to two hours, may be painful and is often costly with noticeable regression beginning in about seven days after the treatment. Improved whitening results are experienced in a professional setting using white light in the 300-990 nm range, but this procedure may be costly and time consuming. Over-the-counter products suffer from other deficiencies, such as difficulty of use, irritation to the soft tissue and the root surfaces and the results usually take up to 14 days. Often, there is only minimal improvement. The consumer needs a customizable whitening alternative that yields results similar to professional whitening, but at the convenience of the home.

Dentist-supervised tooth whitening involves the controlled use of carbamide or hydrogen peroxide, tailored to a particular patient. Dentists may administer in-office treatments or at-home treatments. Before the tooth whitening treatment, most dentists clean the teeth, fill cavities, and ensure the patient's gums are healthy.

Most in-office tooth whitening systems use 15 to 35 percent hydrogen peroxide gels, coupled with a high intensity light to expedite the bleaching chemical reaction.

The in-office whitening procedure involves the dentist gently cleaning the teeth with pumice and then applying a protective barrier on the gums. The dentist then applies hydrogen peroxide paste on the teeth for 15-20 minutes, rinses the hydrogen peroxide off, and usually reapplies hydrogen peroxide 3-4 times. The procedure can achieve about four to six shades of whitening after one 60-80 minute treatment and the patient often times experiences electric-type pain called zingers due to the long exposure to the light and heat.

The other professionally administered whitening technique is the at-home tray and gel system. This will often use 10 to 20 percent carbamide peroxide gels that also contain glycerin, carbomer, sodium hydroxide, water, and flavoring agents. Some gels that contain more than 10 percent carbamide peroxide will also include sodium fluoride to reduce sensitivity and strengthen teeth.

To begin the at-home procedure, the dentist takes impressions (molds) of the mouth, and then has soft, custom mouth trays made. In administering treatment, the user places a thin ribbon of the gel into the tray and wears it for two hours during the day, or while sleeping. Most whitening occurs in one to two weeks. In difficult cases, trays may need to be worn for up to six weeks. Since the peroxide gel is placed into the custom mouth tray and then seated into the mouth, the gel moves onto the roots of the teeth and the soft tissues of the mouth, causing sensitivity in the majority of users.

A combination of in-office and at-home systems can achieve up to 5-7 shades of whitening. Such a procedure is considered safe and effective when monitored by a dentist.

Dentist supervised systems have advantages and disadvantages when compared to over-the-counter tooth whitening products. The main advantage of the dentist supervised system is that the dentist can determine if tooth whitening should be performed and if it will be effective for the patient. Patients with decayed teeth, infected gums, white spots on their teeth, and multiple tooth colored fillings or crowns (caps) on the front teeth may not be good candidates for tooth whitening.

The dentist can also help decide what type of tooth whitening is required (in-office, at-home or both) and the concentration of the whitening gels. The dentist can monitor and treat patients who experience sensitivity to the whitening agents and modify the procedure for those who are having difficulty getting optimal results. Finally, the dentist can help the patient explore porcelain or resin veneers, tooth colored fillings, gum lifts and tooth shaping used with or without tooth whitening. With the help of the dentist, the patient's cosmetic dental goals may be more easily attained.

The disadvantages of dentist supervised whitening systems include higher cost and longer time required to get started and a high level of sensitivity for both the in-office professional whitening and the at-home tray and gel technique. The in-office and at-home tooth whitening systems can cost between $300-$1,000 (sometimes more). In most cases, at-home systems cost less than the in-office systems. With the dentist supervised systems, there may be a wait to get started. You have to schedule an appointment, wait to be seen and evaluated, and then be treated.

Whitening results are best achieved when there is high frequency of use of the whitening agent, in a safe manner without high concentrations of whitening agents that can burn the gum tissue. By increasing the frequency of the whitening by giving the consumer the ability to whiten at home, the regression of the whitening is greatly reduced or even eliminated. That is, high frequency of use and low intensity peroxide gels are more desirable than low frequency of use and high intensity peroxide gels.

It is desired to provide a whitening device (mouthpiece) that is coupled with a delivery system of the whitening gel and an adhesive that keeps a photosensitive agent, such as carbamide or hydrogen peroxide, targeted to the area to be whitened, i.e. to the tooth surface. Such a whitening device preferably causes no harmful breakdown by-products, and is hygienically delivered in a single dose.

Further, it is desired to have an adjustable whitening device (mouthpiece) to accommodate a broad range of different size sets of upper or lower teeth of users. It is further desired that the whitening device seal off the area in the mouth to be treated to reduce the amount of oxygen escape, thus having more oxygen molecules bombard the surface of the tooth for whitening.

In addition, harmful bacteria responsible for causing gum disease in the mouth, specifically, the gram negative anaerobic bacteria, are killed by exposure to electromagnetic radiation in the form of ultraviolet light and heat over 50 degrees C. It would therefore be desirable for a consumer to expose such bacteria to ultraviolet light and heat as well.

SUMMARY OF THE INVENTION

One aspect of the invention resides in an intra-oral whitening device or mouthpiece suited to create a whitening and heat effect to increase a reaction rate of a photosensitive agent, such as carbamide or hydrogen peroxide gel. The person whose teeth are to be whitened can wear the device and whiten his/her teeth without the need of a professional office in a safe, effective, convenient and economical fashion.

The intra oral whitening device (or mouthpiece) of the present invention allows whitening teeth in the convenience of one's home with LED-based white light technology and heat resistors and to customize the whitening procedure safely and effectively without the need for a dentist. The mouthpiece adjusts its orientation manually to accommodate a broad range of different size sets of upper or lower teeth of users and to seal a treatment area in the mouth against exposure to oxygen. The design of the mouthpiece allows for a universal size to fit all people due to the flexible circuit that houses the LEDs and the heat resistors. Additionally, the warming heat from the heat resistors helps the TPR rubber, or silicone mouthpiece to conform to the user's mouth anatomy, thus creating a sealed environment that prevents oxygen escape for whitening and creates more efficient whitening. This creates less wear time and thus less sensitivity during the whitening process. Additionally, the heat generated from the resistors is specifically to ramp up to 52 degrees C. as the 4 eight minute applications are done by the user. This prevents the high heat and high exposure seen in professional whitening lights, and thus much lower sensitivity. Instead of 4 twenty minute applications of the professional whitening as a "one time shot," in this invention, there are 4 eight minute applications that are done over a number of days in a row.

Another aspect of the invention is to expose harmful bacteria in the mouth to electromagnetic radiation, such as ultraviolet light and heat. By doing so, the spread of gum disease caused by the harmful bacteria, such as gram negative anaerobic bacteria, is halted because the ultraviolet light and the warming heat above 50 degrees C. kills the harmful bacteria. Additionally, the bacteria that causes bad breath also lives without oxygen in the nooks and crannies of the tongue and between the teeth. Once exposed to oxygen, these gram negative anaerobic bacteria are killed by the oxygen and the sealed environment of the mouthpiece.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

During a teeth-whitening treatment in a dental office, a whitening gel is applied to the teeth and a protective barrier is placed on the gums, the mucosa and lips to prevent burning of the tissues by the high concentration of hydrogen peroxide in the whitening gel. A leading edge of the whitening gel is placed on a tooth surface. An LED-based white light is placed a few inches from a tooth surface to help activate free radical oxygen, most of which becomes lost into the air. In this invention, the mouthpiece seals or encloses a photosensitive agent, such as carbamide or hydrogen peroxide gel, to prevent the loss of the active electrons of the photosensitive agent (carbamide or hydrogen peroxide) into the air.

The mouthpiece holds LED-based white light sources and alternating heat resistors. A power source, which may be remote from the mouthpiece, is in electrical connection with the LED-based white light sources and heat resistors via a wire. The power source energizes the LED-based white light sources and heat resistors which generate light rays and a warming heat. The light rays strike the tooth surface on the front and the edge and the back of the edge, i.e., in all directions, while the mouthpiece is in its intended position relative to the tooth surface.

Further, a "closed system" created by the mouthpiece or guard that seals or encloses (against exposure to the atmosphere) is efficient for keeping the active free radical oxygen in close proximity to the teeth to enable their movement onto the tooth surface to breakdown the color pigments inside the tooth. A much lower concentration of the carbamide or hydrogen peroxide gel may be used in comparison to what would be needed to achieve like results in an "open system" that did not seal or enclose the photosensitive agent (carbamide or hydrogen peroxide) from exposure to atmosphere.

Indeed, the whitening device (mouthpiece) of the present invention may be used for seven to ten consecutive days with little to no sensitivity to the teeth and gums. This seven to ten consecutive day use constitutes a higher frequency of use than is available in conventional professional whitening techniques and helps avoid a regression phenomenon that has been observed in the professional whitening technique.

The mouthpiece 10 adjusts to a broad range of user dental arch sizes (curvature attributed to lower or upper sets of teeth). It also distributes light and heat in a controlled and focused fashion and provides a means of sealing an area being treated from exposure to oxygen. The heat generated from the alternating heat resistors molds the thermoplastic material of the mouthpiece, i.e., TPR rubber or medical grade silicone, to the user's anatomy and creates the closed system around the formulations, preventing oxygen escape, and thus lower wear time, and thus lower sensitivity for the user.

Figure 1:
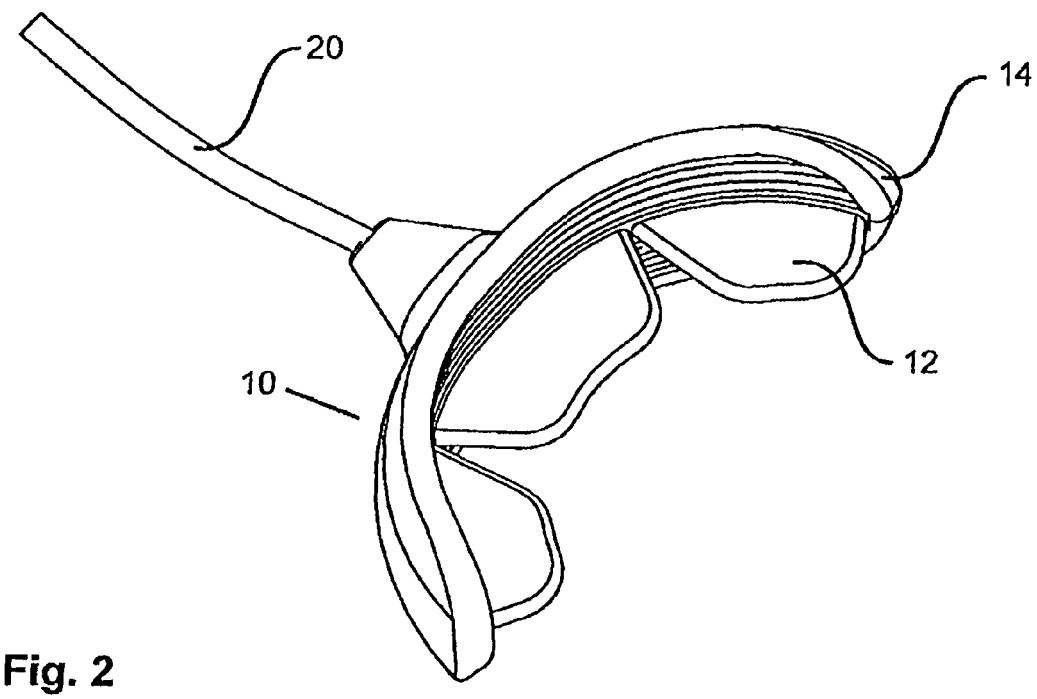
FIG. 1 is an isometric view of a dental mouthpiece in accordance with the invention.
Figure 2:
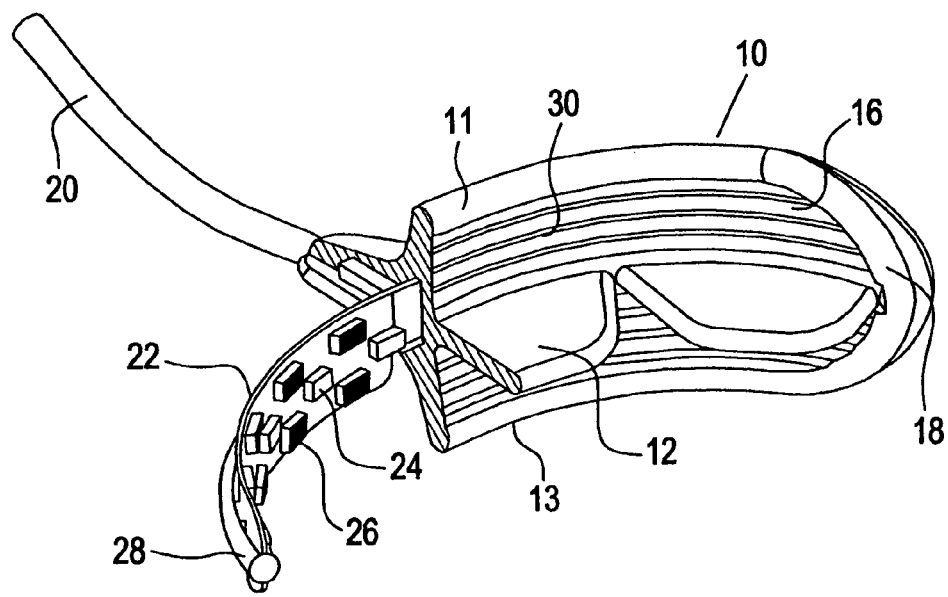
FIG. 2 is a partially broken isometric view of the dental mouthpiece of FIG. 1.
Figure 4:
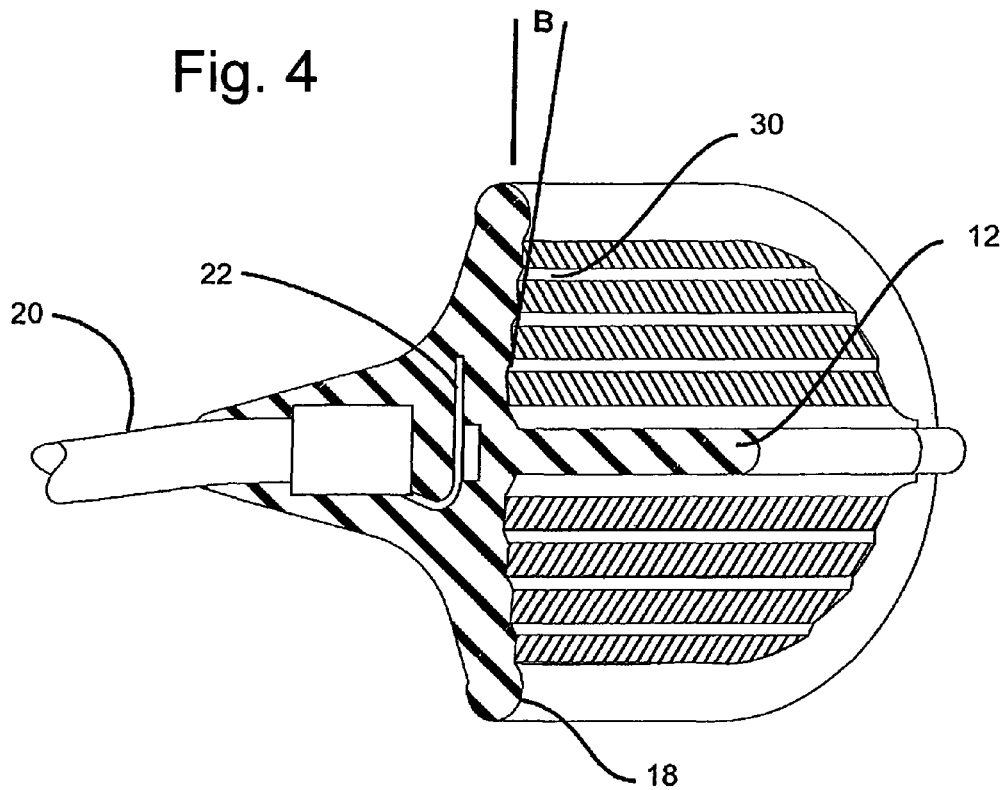
FIG. 4 is a cross-section through a centerline of the dental mouthpiece of FIG. 1.

Referring to FIGS. 1 and 2, the mouthpiece 10 includes upper and lower edges 11, 13 (FIG. 2) and a bite surface 12 formed of segments. The bite surface 12 is perpendicular to the main body 14. The bite surface is also central with respect to the main body 14, with substantially equal portions of the main body 14 above and below the bite surface 12 as seen in FIGS. 2 and 4.

Referring to FIG. 2, the mouthpiece 10 is formed of a clear, elastomeric, molded outer shape 14 that encases a flexible circuit board 22, light emitting diodes 24 and heat generating resistors 26. There is a deformable frame 28 that holds the circuit board 22 during fabrication and may be bent by the user to adjust the orientation of the mouthpiece 10 to set the arch for comfort in the user's mouth. The bite surface 12 is preferably segmented as shown in FIG. 1 to help facilitate the adjustability of the mouthpiece 10 to mouths of differing dimensions. Additionally, adjustability of the mouthpiece 10 to the shape of the arch of the user is facilitated when the heat generating resistors 26 are activated. This is because the heat so generated softens the mouthpiece 10 and increases its malleability, thereby allowing it to be bent and flexed to conform to the particular configuration of the user's arch.

Figure 5:
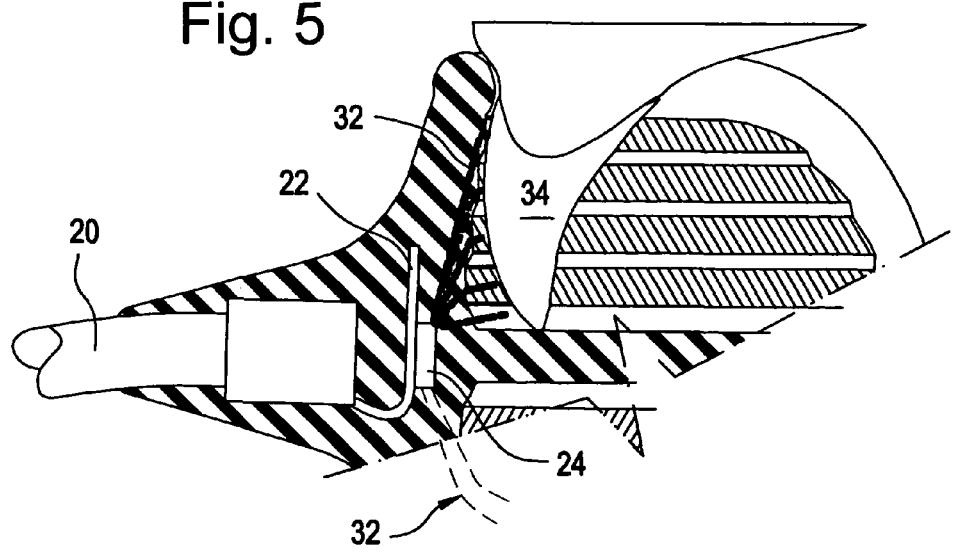
FIG. 5 is cross-section of the dental mouthpiece of FIG. 1 with respect to a user's tooth.

A series of super bright light emitting diodes (LEDs) 24 and heat generating resistors 26 are arrayed on an inner, lingual side of the flexible circuit board 22. The power cord 20 is centrally attached to the outer surface. Looking at FIG. 2, there are 3 rows of elements, with the top and bottom rows preferably entirely including heat generating resistors 26 and with the middle row preferably entirely consisting of LEDs 24. As shown in FIGS. 4 and 5, the LEDs 24 are preferably coplanar with the bite surface 12.

A parallel series of textured bands 16, whose surface texture resembles elongated convex surfaces configured to channel LED light, are formed on the lingual side of the outer shape 14 for the purposes of LED light diffusion over the surface of the tooth being treated.

Figure 3A:
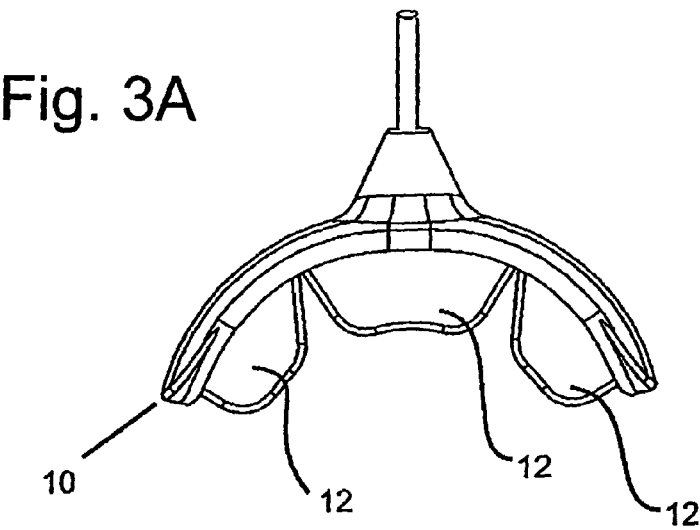
FIGS. 3A-3C are top views of the dental mouthpiece of FIG. 1 that illustrate how the dental mouthpiece is adjusted to open from the position reflected by FIG. 3A to that of FIG. 3B and to close from the position reflected by FIG. 3A to that of FIG. 3C.
Figure 3B:
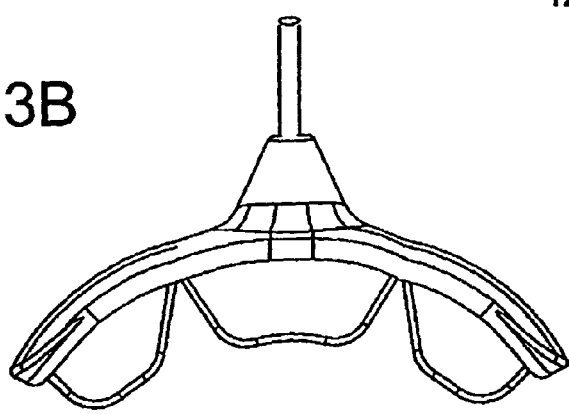
Figure 3C:
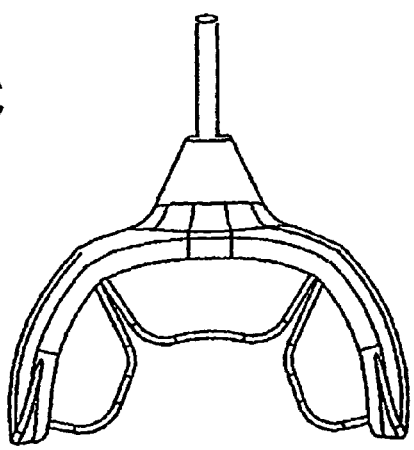

Referring to FIG. 3A, areas between the segmented bite surfaces 12 allow the device to open as in FIG. 3B or close as in FIG. 3C.

Referring to FIG. 4, an inner surface 30 of the mouthpiece 10 tilts inward at an angle of 5 to 15 degrees as noted by B to seal the seal bead 18 and borders the edge of the mouthpiece 10.

Referring to FIG. 5, the inward tilt of the inner surface 30 allows the seal bead 18 to contact the gum above the tooth. This contact provides a barrier seal to both retain the whitening gel and to prevent oxygen from entering the treatment area of the tooth (that is to be treated with the whitening gel).

The light 32 emitted by the LEDs 24 is guided and directed to more evenly illuminate the surface of the teeth 34 by the textured bands 16. The texture of the textured bands 16 provides surfaces that are closer to perpendicular to the light path and less reflective than the generally polished surface of the mouthpiece. The light 32 emitted by the LEDs 24 is directed through the clear material of the main body 14 into both the spaces above and below the bite surface 12 as shown in FIG. 5.

While the foregoing description and drawings represent the preferred embodiments of the present invention, it will be understood that various changes and modifications may be made without departing from the spirit and scope of the present invention.

What is claimed is:

1. A mouthpiece that is adjustable to user arch sizes in order to seal the mouth, comprising:
   a main body made of a clear material and having upper and lower edges, the main body containing a deformable frame, said frame holding a flexible circuit board encased within said main body, the deformable frame being configured to bend under manual force to adjust an orientation of the main body to define an arch configuration;
   a bite surface central to the main body between said upper and lower edges to define a space above the bite surface partly bordered by a first part of the main body and a space below the bite surface partly bordered by a second part of the main body, said bite surface extending outward from the main body;
   a plurality of light emitting elements and heat generating elements arranged in an array on the flexible circuit board, the heat generating elements being separate from the light emitting elements, the light emitting elements being arranged in a row which is coplanar with the bite surface, the light emitting elements and heat generating elements being encased within said clear material of said main body with light from said light emitting elements being emitted through said clear material of said main body; and a plurality of textured bands formed on a lingual side of the main body for directing light from the row of light emitting elements into both spaces above and below the bite surface.

2. The mouthpiece of claim 1, wherein the plurality of light emitting elements and heat generating elements are on a lingual side of the flexible circuit board.

3. The mouthpiece of claim 1, further comprising a power cord attached to a central region of an outside facing surface of the flexible circuit board.

4. The mouthpiece of claim 1, wherein the plurality of textured bands comprises a parallel series of textured bands extending laterally across said main body to diffuse light from the light emitting elements toward areas to be treated.

5. The mouthpiece of claim 4, wherein the mouthpiece includes a polished surface, the series of textured bands are arranged to guide and direct the light from the light emitting elements so as to more evenly illuminate surfaces of teeth than would otherwise be the case without the series of textured bands being present, the series of textured bands having a surface texture that is closer to being perpendicular to a path of the light and less reflective than the polished surface of the mouthpiece.

6. The mouthpiece of claim 1, wherein the bite surface is segmented into a plurality of spaced apart segments that allow room for the deformable flame to flex to selectively re-orient a configuration of the main body between open and closed positions.

7. The mouthpiece of claim 1, wherein the mouthpiece has an inner surface that inwardly tilts within an angular range of 5 to 15 degrees to seal a seal bead, which forms an edge of the mouthpiece.

8. The mouthpiece of claim 7, wherein the inner surface inwardly tilts to allow the seal bead to contact a gum above a tooth, the contact providing a barrier seal to both retain a whitening gel and to prevent oxygen from entering an area of the tooth to be treated by the whitening gel.

9. The mouthpiece of claim 1, wherein the light emitting elements are light emitting diodes.

10. The mouthpiece of claim 1, wherein the heat generating elements are heat generating resistors.

11. The mouthpiece of claim 1, wherein the plurality of textured bands comprises a parallel series of textured bands arranged on an outer surface of the main body.

12. The mouthpiece of claim 11, wherein the series of bands have a surface texture comprising an elongated convex surface configured to channel light from the light emitting elements.

13. The mouthpiece of claim 1, wherein the heat generating elements are arranged in a second row on the circuit board above the row of light emitting elements and in a third row on the circuit board below the row of light emitting elements.

14. The mouthpiece of claim 1, wherein each of the first and second parts of the main body have an inner surface that inwardly tilts within an angular range of 5 to 15 degrees.

15. The mouthpiece of claim 14, further comprising a seal bead that forms an edge of the mouthpiece above, below and around the bite surface.

16. The mouthpiece of claim 1, wherein the bite surface is segmented into a plurality of segments having a first state in which the mouthpiece is open and the bite surface segments are spaced farthest apart from one another, a second state in which the mouthpiece is closed and the bite surface segments are spaced closest to one another and at least one additional state between the first and second states.

17. A mouthpiece that is adjustable to user arch sizes in order to seal the mouth, comprising:
   a main body made of a clear material and having upper and lower edges;
   a deformable frame arranged in the main body, said frame holding a flexible circuit board encased within said main body, the deformable frame being configured to bend under manual force to adjust an orientation of the main body to define an arch configuration;

a bite surface that extends outward from the main body, the bite surface being central to the main body between said upper and lower edges to define a space above the bite surface partly bordered by a first part of the main body and a space below the bite surface partly bordered by a second part of the main body;

a plurality of light emitting elements and heat generating elements arranged in an array on a lingual side of the flexible circuit board, the plurality of light emitting elements arranged in a row which is coplanar with the bite surface, and the heat generating elements being in rows separate from the row of the light emitting elements; and a seal bead that forms an edge of the mouthpiece above, below and around the bite surface, whereby said main body is adjustable to an arch size of a user to enable manual adjustment of said main body to bring said seal bead substantially into contact with the user, the light emitting elements and heat generating elements being encased within said clear material of said main body with light from said light emitting elements being emitted through said clear material of said main body;

and a plurality of textured bands formed on a lingual side of the main body for directing light from the row of light emitting elements into both spaces above and below the bite surface.

18. The mouthpiece of claim 17, wherein the plurality of bands have a surface texture comprising an elongated convex surface configured to channel light from the light emitting elements.

19. The mouthpiece of claim 17, wherein each of the first and second parts of the main body have an inner surface that inwardly tilts within an angular range of 5 to 15 degrees, and the bite surface is segmented into a plurality of segments having a first state in which the mouthpiece is open and the bite surface segments are spaced farthest apart from one another, a second state in which the mouthpiece is closed and the bite surface segments are spaced closest to one another and at least one additional state between the first and second states.

* * * * *